United States Patent
Miyashita et al.

(10) Patent No.: US 10,065,321 B2
(45) Date of Patent: Sep. 4, 2018

(54) ROBOT SERVICE COOPERATION SYSTEM, PLATFORM AND METHOD

(71) Applicant: Advanced Telecommunications Research Institute International, Kyoto (JP)

(72) Inventors: Takahiro Miyashita, Kyoto (JP); Koji Kamei, Kyoto (JP); Kazuhiko Shinozawa, Kyoto (JP); Norihiro Hagita, Kyoto (JP); Tadahisa Kondo, Kyoto (JP)

(73) Assignee: Advanced Telecommunications Research Institute International, Kyoto (JP)

( * ) Notice: Subject to any disclaimer, the term of this patent is extended or adjusted under 35 U.S.C. 154(b) by 197 days.

(21) Appl. No.: 14/780,105

(22) PCT Filed: Mar. 14, 2014

(86) PCT No.: PCT/JP2014/056914
§ 371 (c)(1),
(2) Date: Sep. 25, 2015

(87) PCT Pub. No.: WO2014/156728
PCT Pub. Date: Oct. 2, 2014

(65) Prior Publication Data
US 2016/0046025 A1   Feb. 18, 2016

(30) Foreign Application Priority Data

Mar. 26, 2013   (JP) .................................. 2013-063706

(51) Int. Cl.
*B25J 13/00*   (2006.01)
*B25J 13/08*   (2006.01)
(Continued)

(52) U.S. Cl.
CPC ........... *B25J 13/006* (2013.01); *B25J 11/008* (2013.01); *B25J 13/081* (2013.01);
(Continued)

(58) Field of Classification Search
CPC ....... B25J 13/006; B25J 13/081; B25J 11/008
(Continued)

(56) References Cited

U.S. PATENT DOCUMENTS

| 2005/0256610 | A1* | 11/2005 | Orita | .................... | G05D 1/0088 |
| | | | | | 700/248 |
| 2008/0066065 | A1* | 3/2008 | Kim | ......................... | G06F 8/65 |
| | | | | | 718/1 |

(Continued)

FOREIGN PATENT DOCUMENTS

| EP | 2 434 438 | 3/2012 | ............. G06Q 10/00 |
| JP | 2000-148348 | 5/2000 | ............... G06F 3/00 |

(Continued)

OTHER PUBLICATIONS

A Communication Pursuant to Rule 62 EPC, in English, dated Oct. 7, 2016, enclosing an extended European Search Report which includes the Supplementary Search Report, the European Search Opinion and Annex to the European Search Report, in English, dated Sep. 29, 2016, each of which was issued by the European Patent Office in Applicant's corresponding European Patent Application No. 14774107.8, filed on Mar. 14, 2014.

(Continued)

*Primary Examiner* — Michael Collins
(74) *Attorney, Agent, or Firm* — Bodner & O'Rourke, LLP; Gerald T. Bodner; Christian P. Bodner

(57) ABSTRACT

A robot service cooperation system (10) includes a server (12), a mobile terminal (14) and various robots (16a-16c) respectively connected to a network (100). Each of applications (A1, A2, A3, - - - ) on the network is written with (Continued)

cooperation information indicating that which other application can be cooperated with. A CPU (20) of the server specifies (S3) at least based on the cooperation information a plurality of cooperable services that can be provided to a user of the mobile terminal, presents (S7) the specified plurality of services to the user and makes (S13) the user select an arbitrary combination, and makes (S17, S19) a plurality of services constituting the selected combination cooperate mutually by registering at least a start condition of each service into an event queue in association with at least an end event of another service.

6 Claims, 12 Drawing Sheets

(51) Int. Cl.
*G06Q 30/06* (2012.01)
*B25J 11/00* (2006.01)
*G06Q 10/10* (2012.01)
*G06Q 50/02* (2012.01)
*G06Q 50/22* (2018.01)

(52) U.S. Cl.
CPC ........... *G06Q 10/101* (2013.01); *G06Q 30/06* (2013.01); *G06Q 50/02* (2013.01); *G06Q 50/22* (2013.01)

(58) Field of Classification Search
USPC ........................................................ 700/264
See application file for complete search history.

(56) References Cited

U.S. PATENT DOCUMENTS

| | | | |
|---|---|---|---|
| 2010/0094459 A1* | 4/2010 | Cho | ..................... G05D 1/0291 700/248 |
| 2011/0241882 A1 | 10/2011 | Gonzales et al. | .......... 340/572.1 |

FOREIGN PATENT DOCUMENTS

| | | | | |
|---|---|---|---|---|
| JP | 2004-258809 | 9/2004 | ............. | G06F 13/00 |
| JP | 2005-111637 | 4/2005 | ............. | B25J 13/00 |
| JP | 2005-324278 | 11/2005 | ............. | B25J 13/00 |
| JP | 2006-011650 | 1/2006 | ............. | G06F 21/20 |
| JP | 2007-274601 | 10/2007 | ............. | H04M 11/00 |
| JP | 2008-003860 | 1/2008 | ............. | G06Q 50/00 |

OTHER PUBLICATIONS

The International Search Report, in English, dated May 27, 2014, issued from Applicant's corresponding PCT Application No. PCT/JP2014/056914, filed on Mar. 14, 2014, from the World Intellectual Property Organization (WIPO).

* cited by examiner

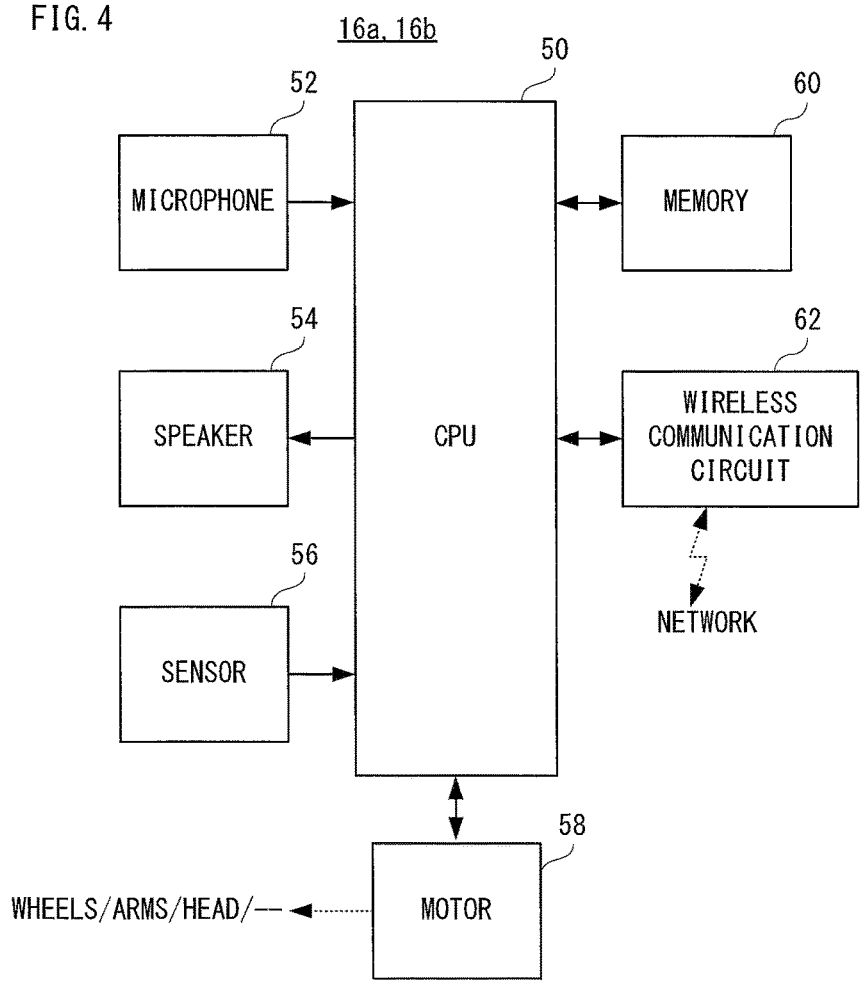

FIG. 7

(USER ATTRIBUTE INFORMATION) 92

| USER (MOBILE TERMINAL) ID | ATTRIBUTE |
|---|---|
| a | WALK IMPAIRED PERSON |
| b | AGED PERSON |
| ⋮ | ⋮ |

FIG. 8

(ROBOT INFORMATION) 94

| ROBOT ID | ATTRIBUTE | FUNCTION | MOVING RANGE |
|---|---|---|---|
| R1 | WHEELCHAIR | WHEELCHAIR, CONVERSATION | WITHIN SHOPPING CENTER |
| R2 | HUMANOID | GUIDE LUGGAGE CARRIER, CONVERSATION | WITHIN SHOPPING CENTER |
| R3 | VIRTUAL (by MOBILE TERMINAL) | HEALTH WATCH, CONVERSATION | WITHIN COMMUNICABLE RANGE OF MOBILE TERMINAL |
| R4 | INVISIBLE (by ENVIRONMENT SENSOR) | HUMAN DETECTION | FIXED AT PREDETERMINED POSITION IN SHOPPING CENTER |
| ⋮ | ⋮ | ⋮ | ⋮ |

FIG. 9

(A) (EVENT QUEUE INFORMATION CORRESPONDING TO SEQUENTIAL MANNER) 84

| SERVICE | START CONDITION |
|---|---|
| SHOPPING SUPPORT | ARRIVED AT SHOPPING CENTER |
| MIGRATION SUPPORT | SHOPPING FINISHED |

(B) (EVENT QUEUE INFORMATION CORRESPONDING TO INTERRUPTION MANNER) 84

| SERVICE | START CONDITION | RESTART CONDITION |
|---|---|---|
| MIGRATION SUPPORT | ARRIVED AT SHOPPING CENTER | SHOPPING FINISHED |
| SHOPPING SUPPORT | MIGRATION INTERRUPTED | — |

(C) (EVENT QUEUE INFORMATION CORRESPONDING TO PARALLEL MANNER) 84

| SERVICE | START CONDITION |
|---|---|
| SHOPPING (OR MIGRATION) SUPPORT | ARRIVED AT SHOPPING CENTER |
| HEALTH WATCH | SHOPPING (OR MIGRATION) STARTED |

(D) (EVENT QUEUE INFORMATION CORRESPONDING TO SEQUENTIAL AND PARALLEL MANNER) 84

| SERVICE | START CONDITION |
|---|---|
| SHOPPING SUPPORT | ARRIVED AT SHOPPING CENTER |
| MIGRATION SUPPORT | SHOPPING FINISHED |
| HEALTH WATCH | SHOPPING STARTED |

(E) (EVENT QUEUE INFORMATION CORRESPONDING TO INTERRUPTION AND PARALLEL MANNER) 84

| SERVICE | START CONDITION | RESTART CONDITION |
|---|---|---|
| MIGRATION SUPPORT | ARRIVED AT SHOPPING CENTER | SHOPPING FINISHED |
| SHOPPING SUPPORT | MIGRATION INTERRUPTED | — |
| HEALTH WATCH | MIGRATION STARTED | — |

(PRESENT TO USER COOPERABLE SERVICES)

(SELECTION OF COMBINATION BY USER)

(A) SHOPPING SUPPORT | MIGRATION SUPPORT | HEALTH WATCH (B) SHOPPING SUPPORT | MIGRATION SUPPORT | HEALTH WATCH (C) SHOPPING SUPPORT | MIGRATION SUPPORT | HEALTH WATCH (D) SHOPPING SUPPORT | MIGRATION SUPPORT | HEALTH WATCH

ROBOT SERVICE COOPERATION SYSTEM, PLATFORM AND METHOD

FIELD OF ART

The present invention relates to a robot service cooperation system, platform and method, and more specifically, a robot service cooperation system, platform and method, capable of providing services to a user in various places by using a robot connected to a network.

BACKGROUND ART

As such a kind of conventional system, a system disclosed in the patent literature 1, for example is known. In a system of this background art, one or two or more robots that are arranged in a space, a robot router for controlling the robots and a space manager that performs status control of the robots in the space and collects and manages environment information are connected via a communication network, and if a user registers a user attribute into the robot router, the system controls the robot in a space that the robot router exists based on the user attribute and the environment information that are held in the robot router, thereby to provide a service. The user can receive the most suitable service in the latest environment by thus connecting the user attribute and the environment information with each other.
Patent literature 1: Japanese Patent Application Laying-open No. 2005-111637

SUMMARY OF THE INVENTION

Problem to be Solved by the Invention

However, it was only a single service that the user can receive by the background art.

Therefore, it is a primary object of the present invention to provide a novel robot service cooperation system, platform and method.

It is another object of the present invention to provide a robot service cooperation system, platform and method capable of providing a plurality of services that a user needs by making the services cooperate mutually.

Means for Solving the Problem

The present invention employs following features in order to solve the above-described problem. It should be noted that reference numerals inside the parentheses and the supplements show a corresponding relationship with embodiments described later for easy understanding of the present invention, and do not limit the present invention.

A first invention is a robot service cooperation system (10) that includes a server (12) connected to a network (100), a mobile terminal (14) connected to the network and a robot (16a-16c) connected to the network, and makes a plurality of services cooperate mutually, the plurality of services being respectively provided to a user of the mobile terminal (14) by a plurality of applications software (A1-A3) on the network by using the robot (16a-16c), wherein cooperation information indicating which another application software can be cooperated with is described in each of the applications software (FIG. 5), and the server comprises a specifying module (S3) operable to specify a plurality of cooperable services that can be provided to the user of the mobile terminal at least based on the cooperation information described in each of the service applications software; a presentation selection module (S7, S13: FIG. 14-FIG. 16) operable to present to the user of the mobile terminal a plurality of services that are specified by the specifying module and make the user select an arbitrary combination of the services; and a cooperation module (S17, S19: FIG. 9(A)-FIG. 9(E)) operable to make a plurality of services constituting the combination that is selected by the presentation selection module cooperate mutually by registering at least a start condition of each of the plurality of services into an event queue in association with at least an end event of another service.

Although the presentation selection module performs presentation and selection via a touch screen of the mobile terminal (14) in a certain embodiment, it may utilize in other embodiments a voice output function and a voice recognition function of the mobile terminal or the robot.

According to the first invention, it becomes possible to provide a plurality of services that the user needs with making the services cooperate mutually in at least a sequential manner.

A second invention is the robot service cooperation system according to the first invention, wherein the presentation selection module includes an input module (S13: FIG. 16) operable to make the user of the mobile terminal further input information relevant to the selected combination, and the cooperation module is operable to register, when the input module inputs information that it is possible to determine that a first service and a second service should be sequentially performed, a start condition of the second service in association with an end event of the first service (FIG. 9(A)) based on the information concerned.

An end/interruption event of the service is issued from the application software that provides the service concerned, for example. Otherwise, the event may be issued from the mobile terminal according to an operation by the user.

According to the second invention, it is possible to provide two services that the user needs with making the services cooperate mutually in a sequential manner.

A third invention is the robot service cooperation system according to the second invention, wherein the cooperation module is operable to register, when the input module inputs information that it is possible to determine that the second service should be performed with interrupting performance of the first service, a start condition of the second service in association with an interruption event of the first service and a restart condition of the first service in association with an end event of the second service (FIG. 9(B)) based on the information concerned.

According to the third invention, it is possible to provide the two services that the user needs, with making the services cooperate mutually in a manner that the user desires among the sequential manner and a parallel manner.

A fourth invention is the robot service cooperation system according to the second invention, wherein it is described in the cooperation information of a specific application software (A3) that the application software concerned can cooperate with any further application software (A1, A2) in a parallel manner, and the cooperation module is operable to register, when the service provided by the specific application software is included in the plurality of services that constitute the combination selected by the selection module, a start condition of the service concerned in association with a start event of the further service (FIG. 9(D), FIG. 9(E)).

According to the fourth invention, it is possible to provide the further service in the parallel manner with making the two services cooperate mutually in the sequential manner or the parallel manner.

A fifth invention is the robot service cooperation system according to the first invention, further comprising a database that is registered with user attribute information (92: FIG. 7) indicating the attribute of the user of the mobile terminal and robot information (94: FIG. 8) indicating at least a function of the robot, wherein the specifying module is operable to perform specifying by referring also to each information in the database.

Each of the information is registered so as to be updatable preferably.

According to the fifth invention, it becomes possible to provide the service using the robot with the function according to the attribute of the user.

A sixth invention is the robot service cooperation system according to the fifth invention, wherein the robot information further indicates a moving range of the robot, and further comprising a detection module (46) operable to detect a current position of the user of the mobile terminal, and the specifying module is operable to perform specifying while also taking into consideration a comparison result of a detection result by the detection module and the moving range of the robot.

According to the sixth invention, it becomes possible to provide the service using the robot in various places.

A seventh invention is the robot service cooperation system according to the first invention, wherein the presentation selection module is operable to display a plurality of icons (I1-I3) corresponding to the plurality of services specified by the specifying module on a touch screen (32, 34) of the mobile terminal, and make the user select an arbitrary combination (FIG. 14, FIG. 15), and make display manners mutually differ between a plurality of first icons (I1, I2) constituting the selected combination and a remaining second icon (I3) (FIG. 16) among the plurality of icons being displayed on the touch screen.

According to the seventh invention, it is possible to make the user recognize whether the service is in a selected state or a non-selected state. As a result, the user can know existence of the service that the user has not selected until now, and can also mutually switch the selected state or the non-selected state of each service.

An eighth invention is a robot service cooperation platform (PF) that is implemented by a computer (20) of a server (12) connected to a network (100), and makes a plurality of services cooperate mutually, the plurality of services being respectively provided by a plurality of applications software (A1-A3) on the network to a user of a mobile terminal (14) by using a robot (16a-16c), wherein cooperation information indicating which another application software can be cooperated with is described in each of the applications software (FIG. 5), comprising: a specifying module (S3) operable to specify a plurality of cooperable services that can be provided to the user of the mobile terminal at least based on the cooperation information described in each of the service applications software; a presentation selection module (S7, S13: FIG. 14-FIG. 16) operable to present to the user of the mobile terminal a plurality of services specified by the specifying module and make the user select an arbitrary combination of the services; and a cooperation module (S17, S19: FIG. 9(A)-FIG. 9(E)) operable to make a plurality of services constituting a combination selected by the presentation selection module cooperate mutually by registering at least a start condition of each of the plurality of services in an event queue in association with at least an end event of another service.

A ninth invention is a robot service cooperation method that is performed by a computer of a server connected to a network, and makes a plurality of services cooperate mutually, the plurality of services being respectively provided by a plurality of applications software on the network to a user of a mobile terminal by using a robot, wherein cooperation information indicating which other application software can be cooperated with is described in each of the applications software, comprising steps of: a specifying step operable to specify a plurality of cooperable services that can be provided to the user of the mobile terminal at least based on the cooperation information described in each of the service applications software; a presentation selection step operable to present to the user of the mobile terminal a plurality of services specified in the specifying step and make the user select an arbitrary combination of the services; and a cooperation step operable to make a plurality of services constituting a combination selected in the presentation selection step cooperate mutually by registering at least a start condition of each of the plurality of services in an event queue in association with at least an end event of another service.

According to the eighth and ninth invention, like the first invention, it becomes possible to provide a plurality of services that the user needs with making the services cooperate mutually in at least a sequential manner.

Advantage of the Invention

According to the present invention, it is possible to implement a robot service cooperation system and platform that make a plurality of services that the user needs with making the services cooperate mutually.

The above mentioned objects and other objects, features, aspects and advantages of the present invention will become more apparent from the following detailed description of the present invention when taken in conjunction with the accompanying drawings.

BRIEF DESCRIPTION OF THE DRAWINGS

FIG. 4 is a block diagram showing an example of structure of each of a wheelchair robot and a humanoid robot included in the robot service cooperation system.

FIG. 5 is an illustration view showing an example of application software that provides various robot services on the robot service cooperation system.

FIG. 7 is an illustration view showing an example of user attribute information that is stored in a memory.

FIG. 8 is an illustration view showing an example of robot information that is stored in the memory.

FIG. 9 shows examples of event queue information that are stored in the memory, wherein FIG. 9(A) shows event queue information in a case of providing shopping support and migration support in a sequential manner, FIG. 9(B) shows event queue information in a case of providing shopping support and migration support in an interruption manner, FIG. 9(C) shows event queue information in a case of providing shopping support and health watch (or migration support and health watch) in a parallel manner, FIG. 9(D) shows event queue information in a case of further providing health watch in a parallel manner, while providing shopping support and migration support in a sequential manner, and FIG. 9(E) shows event queue information in a case of further providing health watch in a parallel manner, while providing of shopping support and migration support in an interruption manner.

FIG. 14 is an illustration view showing an example of a user interface (UI) that is applied to a touch screen of the mobile terminal, and shows a screen that presents comparable services that can be provided to a user and makes the user select an arbitrary combination.

FIG. 15 is shows selected examples of combination by a user, wherein FIG. 15(A) shows a state where a combination of shopping support and migration support is selected, FIG. 15(B) shows a state where a combination of migration support and health watch is selected, FIG. 15(C) shows a state where a combination of shopping support and health watch is selected, and FIG. 15(D) shows a state where a combination of shopping support, migration support and health watch is selected.

FORMS FOR EMBODYING THE INVENTION

Figure 1:
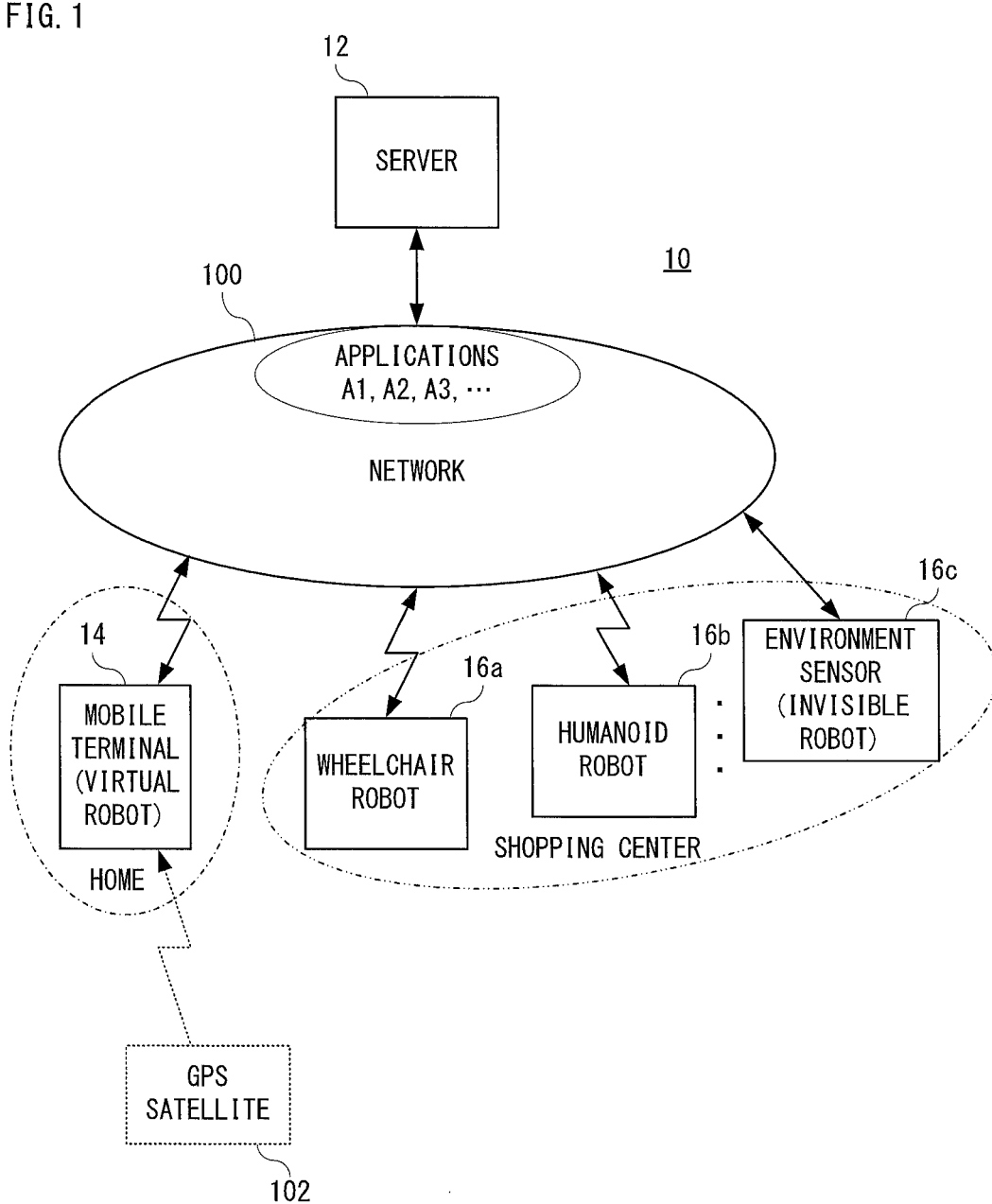
FIG. 1 is a block diagram showing structure of a robot service cooperation system that is an embodiment of a present invention.

Structure of a robot service cooperation system that is an embodiment of the present invention is shown in FIG. 1. With reference to FIG. 1, the robot service cooperation system 10 includes a server 12, and the server 12 is connected with each of a mobile terminal 14, a wheelchair robot 16a, a humanoid robot 16b and an environment sensor 16c via a network 100. The mobile terminal 14 is carried by a user, and the wheelchair robot 16a, the humanoid robot 16b and the environment sensor 16c are stationed in a shopping center that the user does some shopping.

The mobile terminal 14 can detect a current position of itself (that is, a user) based on a signal from a GPS satellite 102, detect a pulse and quantity of motion of the user, and talk with a user through a virtual robot (not shown) in a virtual space.

The humanoid robot 16b has a head, arms, wheels, etc., and can move autonomously in the shopping center while talking with the user with gesture. The wheelchair robot 16a has a chair and wheels, and can move autonomously in the shopping center while talking with the user in a state that the user sits on.

The environment sensor 16c is constituted by a laser range finder, an infrared sensor, an image sensor, etc., and can detect the user (recognize a face and specify a position) without being conscious by the user as an invisible robot that is fixed to predetermined positions (at an entrance, along passage, etc., for example) in the shopping center.

Figure 2:
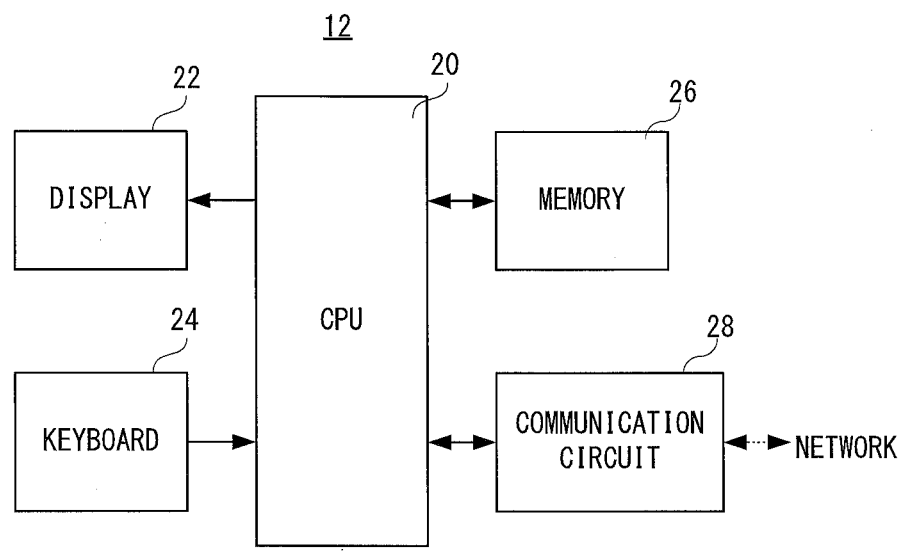
FIG. 2 is a block diagram showing an example of structure of a server included in the robot service cooperation system.

An example of structure of the server 12 is shown in FIG. 2. With reference to FIG. 2, the server 12 comprises a CPU 20, a display 22, a keyboard 24, a memory 26 and a communication circuit 28. The keyboard 24 is operated by the operator, and makes the CPU 20 perform information processing by inputting instructions to the CPU 20. In addition, the operator can also operate each robot (16a, 16b) by remote control. The display 22 displays a result of information processing by the CPU 20. The memory 26 stores programs and data for making the CPU 20 perform information processing. The communication circuit 28 connects the CPU 20 to the network 100 communicably.

Figure 3:
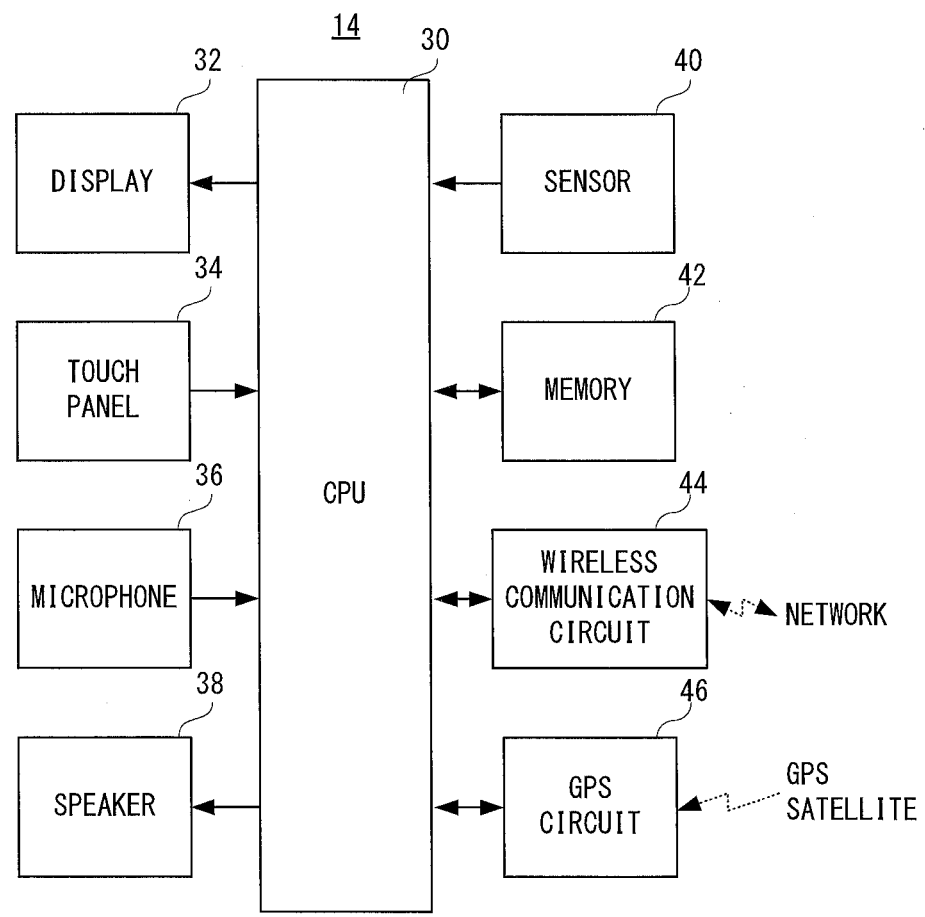
FIG. 3 is a block diagram showing an example of structure of a mobile terminal included in the robot service cooperation system.

An example of structure of the mobile terminal 14 is shown in FIG. 3. With reference to FIG. 3, the mobile terminal 14 comprises a CPU 30, a display 32, a touch panel 34, a microphone 36, a speaker 38, a sensor 40, a memory 42, a wireless communication circuit 44 and a GPS circuit 46. A touch screen is constituted by the display 32 and the touch panel 34, and the CPU 30 presents information to the user and makes the user input (select) through the touch screen. Furthermore, the CPU 30 displays a virtual robot on the display 32, and talks with the user through the microphone 36 and the speaker 38. The sensor 40 is constituted by an acceleration sensor, a gyroscope, etc., and the CPU 30 detects a pulse and quantity of motion of the user based on an output of the sensor 40.

The memory 42 stores programs and data for making the CPU 30 perform the above-described processing. The wireless communication circuit 44 connects the CPU 30 to the network 100 wireless-communicably. The GPS circuit 46 receives signals from a plurality of GPS satellites 102, detects a current position of the mobile terminal 14 (user) based on the received signals, and outputs current position information indicating a detection result.

An example of structure of each of the wheelchair robot 16a and the humanoid robot 16b is shown in FIG. 4. With reference to FIG. 4, the wheelchair robot 16a and the humanoid robot 16b each comprises a CPU 50, a microphone 52, a speaker 54, a sensor 56, a motor 58, a memory 60a and a wireless communication circuit 62. The CPU 50 talks with the user through the microphone 52 and the speaker 54. The sensor 56 is constituted by an image sensor, an infrared sensor, etc., and based on an output of the sensor 56, the CPU 50 controls the motor 58 and detects a user. The motor 58 drives wheels (and further arms/head in a case of the humanoid robot 16b) under control of the CPU 50.

The memory 60 stores programs and data for making the CPU 50 perform the above-described processing. The wireless communication circuit 62 connects the CPU 50 to the network 100 wireless-communicably.

FIG. 5 shows examples of the applications software (hereinafter, "application") A1, A2 and A3 that provide various services in the robot service cooperation system 10 constituted as described above. With reference to FIG. 5, cooperation information ("cooperable with the migration support application", "cooperable with shopping support application" and "cooperable with each application in a parallel manner") is added to each of programs (shopping support program, migration support program and health watch program) of the applications A1, A2 and A3.

More specifically, the application A1 is a shopping support application that provides to a user such as an aged person the shopping support service (guiding to a target shop or store, explaining an item in the shop or carrying a purchased item) using the humanoid robot 16b, and cooperable with a migration support application (A2). The application A2 is the migration support application that provides to a user such as a walk impaired person a migration support service (service to go around with wheelchair in the shopping center while explaining items of respective shops) using the wheelchair robot 16*a*, and cooperable with the shopping support application (A1). The application A3 is the health watch application that provides to a user such as an aged person a health watch service (service to perform advice about health such as "to take break a little" by detecting a pulse and quantity of motion) using the virtual robot (mobile terminal 1), and cooperable with each of the shopping support application (A1) and the migration support application (A2) in a parallel manner.

It should be noted that in this embodiment, "shopping" means a purchase behavior to go to the counter directly because an item want to buy is already decided, and "migration" means a purchase behavior to find an item want to buy while going around inside the shopping center because the item want to buy has not been yet decided.

Figure 10:
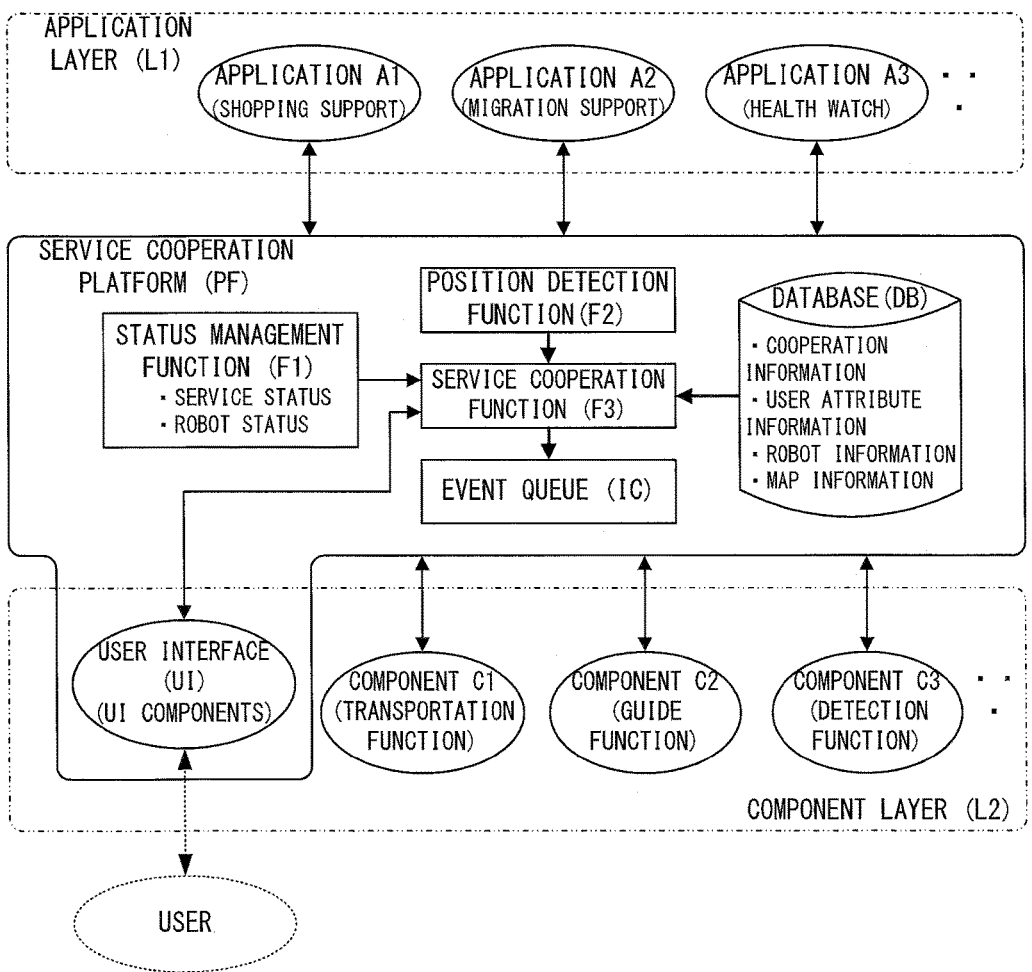
FIG. 10 is a block diagram showing functional structure of a service cooperation platform (PF) that is implemented by a CPU operation of the server.
Figure 11:
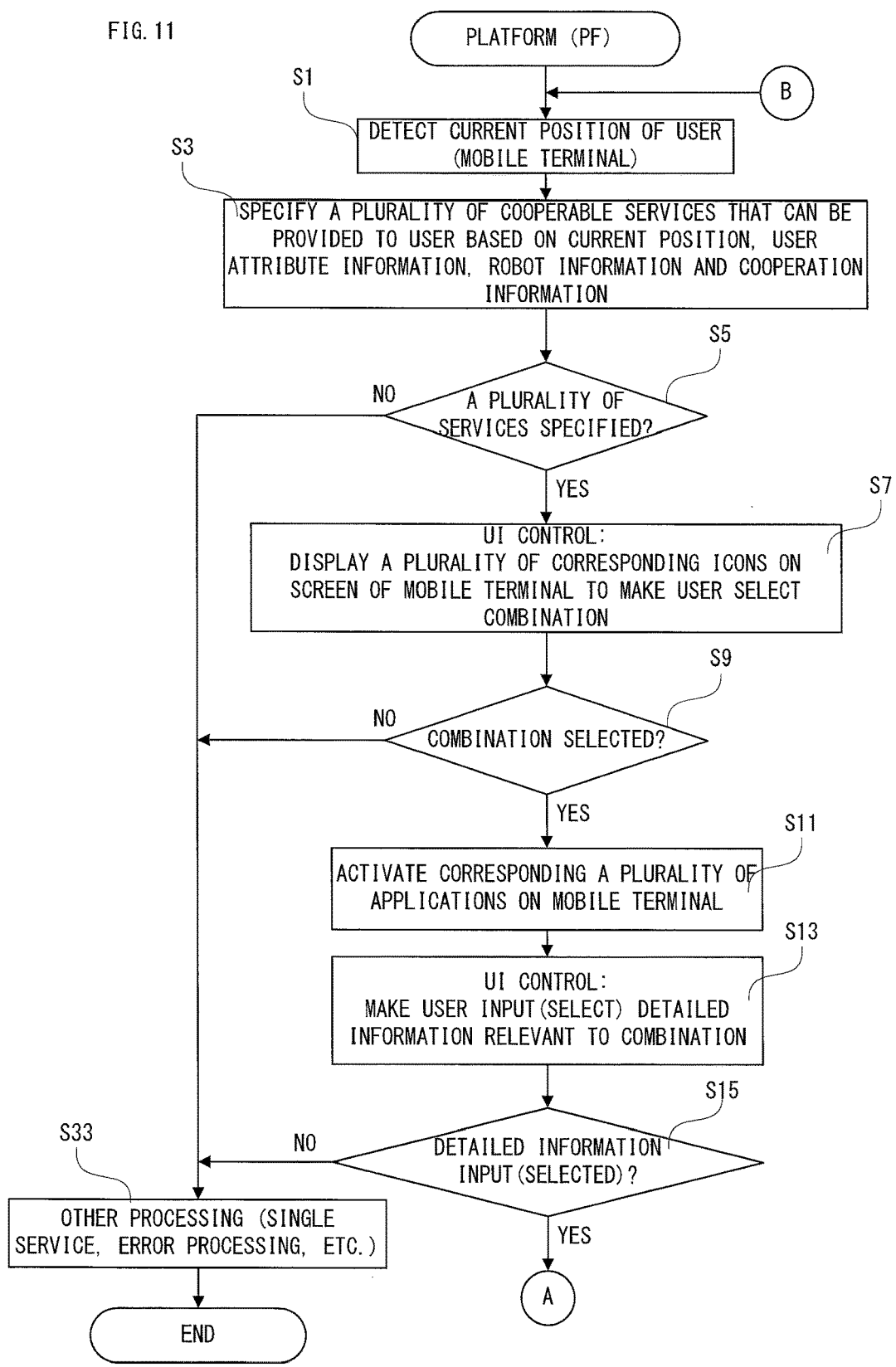
FIG. 11 is a flowchart showing a part of processing (robot service cooperation processing) of the PF.
Figure 12:
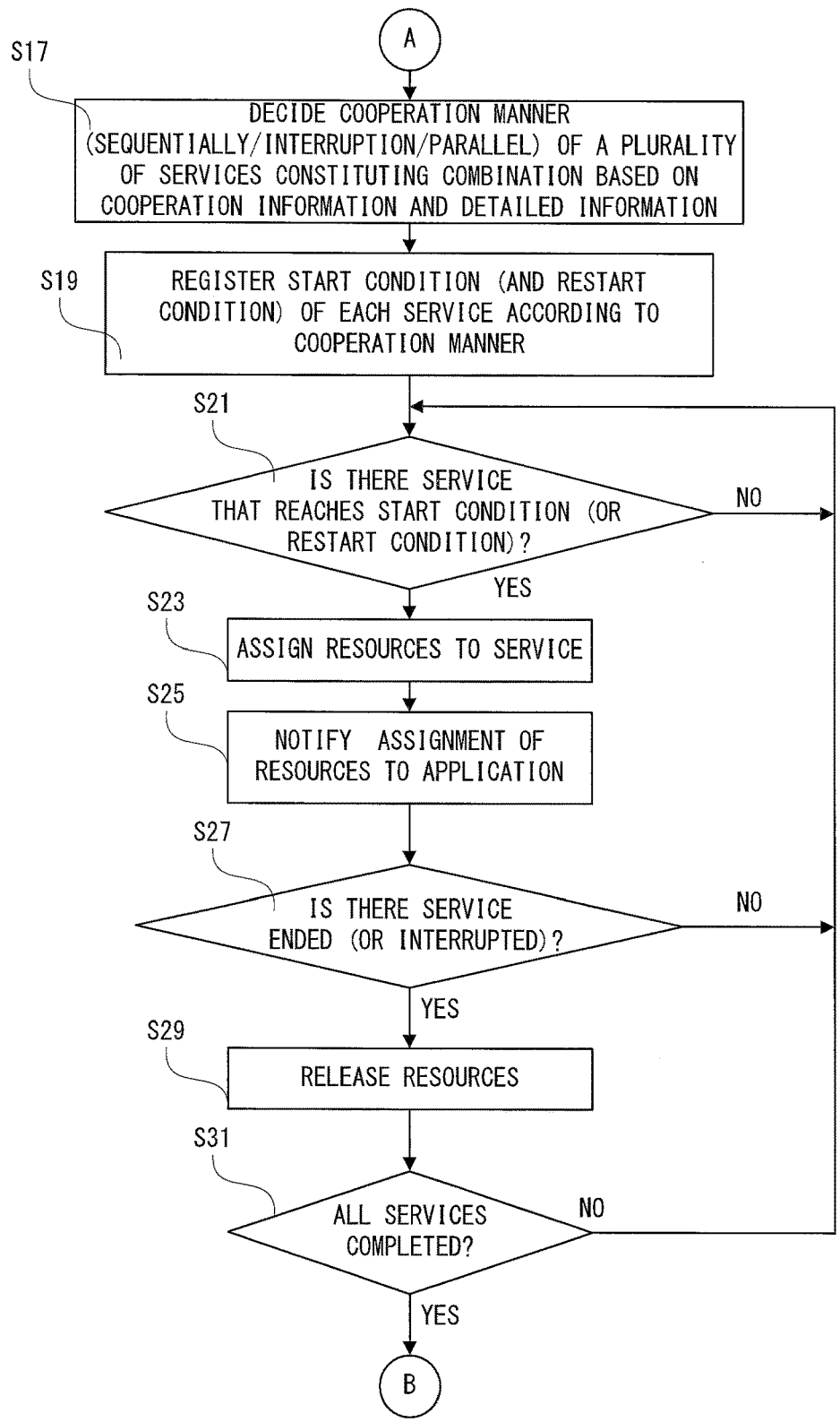
FIG. 12 is a flowchart showing the other part of the robot service cooperation processing.
Figure 13:
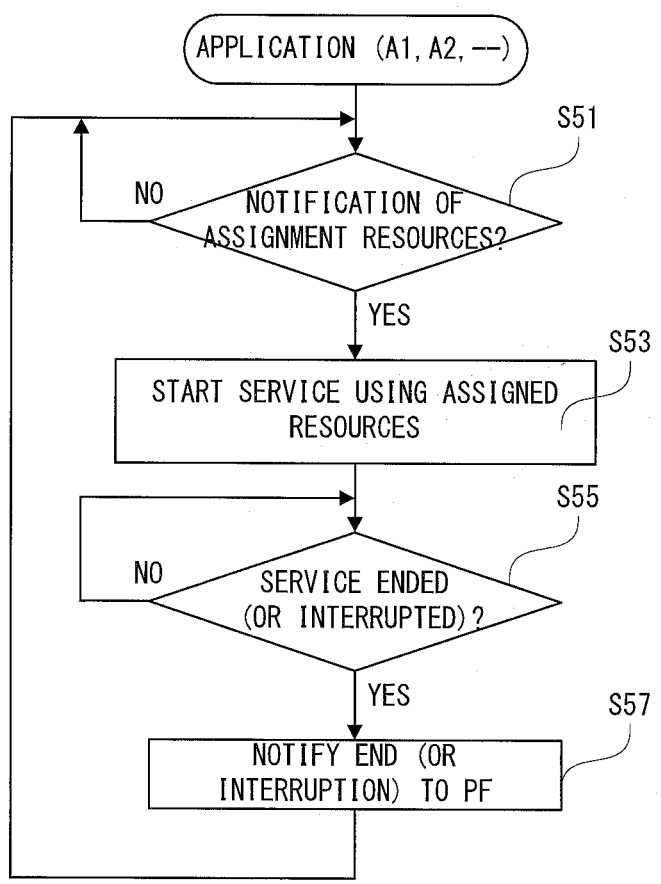
FIG. 13 is a flowchart showing processing (service providing processing) of each application that is implemented by a CPU operation of the server.

In the robot service cooperation system 10, the CPU 20 of the server 12 mainly implements a robot service cooperation platform (abbreviated to "PF" suitably) having functions as shown in FIG. 10 based on programs and data that are stored in the memory 26 as shown in FIG. 6-FIG. 9, and performs the processing according to flowcharts in FIG. 11-FIG. 13, whereby a plurality of services that a plurality of applications respectively provide (for example, arbitrary two or all the three of the shopping support, the migration support and health watch that are provided by three applications shown in FIG. 5) can be provided to the user with making these cooperate mutually.

Figure 6:
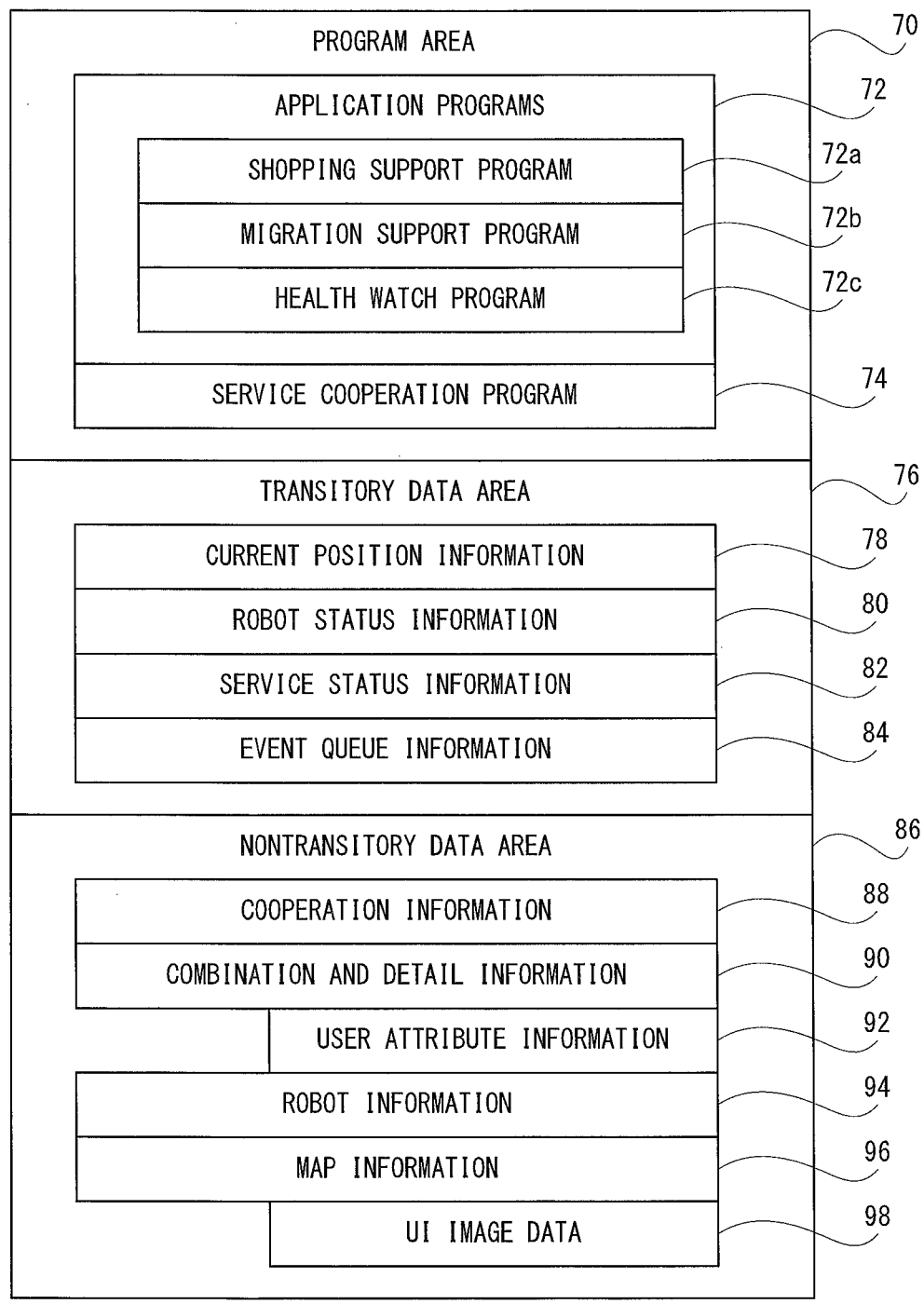
FIG. 6 is a memory map showing contents of a memory of the server.

The contents of the memory 26 are shown in FIG. 6. With reference to FIG. 6, the memory 26 includes a program area 70, a transitory data area 76, and a nontransitory data area 86, and application programs 72 and a service cooperation program 74 are stored in the program area 70.

The application programs 72 are programs for controlling hardware of the robot service cooperation system 10 so as to provide various services to a user, and here, include a shopping support program 72*a*, a migration support program 72*b* and a health watch program 72*c* respectively corresponding to the three applications A1, A2 and A3 shown in FIG. 5. The service cooperation program 74 is a program for making a plurality of services (here, two or three among the three services, shopping support, migration support and health watch) based on the application programs 72 cooperate mutually.

In the transitory data area 76, current position information 78, robot status information 80, service status information 82 and event queue information 84 are stored. The current position information 78 is information indicating a current position of the mobile terminal 14, that is, a user, and uses current position information that is output mainly from the GPS circuit 46 of the mobile terminal 14 itself (may be substituted with current position information acquired from the environment sensor 16*c*, and may use both together).

The robot status information 80 is information indicating states of various robots (14, 16*a*-16*c*) shown in FIG. 1 (for example, in an available state, in a state utilized for any service or the like), and uses information provided by the robot concerned itself.

The service status information 82 is information indicating states (start waiting state, during performance state, interrupted state, ended state, etc.) of a plurality of services (here, the shopping support, migration support and health watch that the three applications of FIG. 5 provide) provided by the applications, and is controlled by the service cooperation program 74 based on event information (start event, interruption event, restart event, end event, etc.) provided from the application concerned itself.

The event queue information 84 is information that is controlled by the service cooperation program 74 in order to make a plurality of services (here, the shopping support, migration support and health watch that the three applications of FIG. 5 provide) provided by the applications cooperate mutually in a sequential manner or interruption manner, or a manner that a parallel manner is used together with the sequential manner or the interruption manner, and has contents shown in FIG. 9, for example.

The event queue information 84 in FIG. 9 (A) is for making the shopping support (first service) and the migration support (second service) cooperate in a sequential manner, and "Arrived at shopping center" is registered as a start condition for the shopping support, and also "Shopping finished" is registered as a start condition for the migration support. Thus, when making the first and second services cooperate in a sequential manner, a start condition of the second service may be registered in association with an end event of the first service. In general, if a start condition of the i-th service is registered in association with an end event of the (i−1)th service, it is possible to make i units of services cooperate in a sequential manner (here, i is an integer greater than or equal to 2).

The event queue information 84 in FIG. 9 (B) is for making the shopping support (second service) and the migration support (first service) cooperate in an interruption manner, and "Arrived at shopping center" is registered as a start condition for the migration support, and also "Migration interrupted" is registered as a start condition for the shopping support, and then "Shopping finished" is registered as a restart condition for the migration support. Thus, when making the first and second services cooperate in an interruption manner, a start condition of the second service may be registered in association with an interruption event of the first service and a restart condition of the first service may be registered in association with an end event of the second service.

The event queue information 84 in FIG. 9 (C) is for making the shopping support (or migration support) and the health watch cooperate in a parallel manner, and "Arrived at shopping center" is registered as a start condition for the shopping support (or migration support) and also "Shopping (or migration) started" is registered as a start condition for the health watch. Thus, when making the first and second services cooperate in a parallel manner, a start condition of the second service may be registered in association with a start event of the first service.

The event queue information 84 in FIG. 9 (D) is for making the shopping support (first service) and the migration support (second service) cooperate in a sequential manner and further making the migration support (third service) cooperate in a parallel manner, and "Arrived at shopping center" is registered as a start condition for the shopping support, and also "Shopping finished" is registered as a start condition for the migration support and "Shopping started" is registered as a start condition for the health watch. Thus, when making the first and second services cooperate in a sequential manner and further making the third service cooperate in a parallel manner, a start condition of the second service may be registered in association with an end event of the first service and a start condition of the third service may be registered in association with a start event of the first service.

The event queue information 84 in FIG. 9 (E) is for making the shopping support (second service) and the migration support (first service) cooperate in an interruption manner and further making the migration support (third service) cooperate in a parallel manner, and "Arrived at shopping center" is registered as a start condition for the migration support and further "Migration interrupted" is registered as a start condition for the shopping support, and in addition to "Shopping finished" is registered as a restart condition for the migration support, "Migration started" is registered as a start condition for the health watch. Thus, when making the first and second services cooperate in an interruption manner and further making the third service cooperate in a parallel manner, in addition to a start condition of the second service may be registered in association with an interruption event of the first service and a restart condition of the first service may be registered in association with an end event of the second service, a start condition of the third service may be registered in association with a start event of the first service.

Returning to FIG. 6, in the nontransitory data area 86, cooperation information 88, combination and detailed information 90, user attribute information 92, robot information 94, map information 96 and UI image data 98 are stored.

The cooperation information 88 is information indicating what kind of cooperation is possible among a plurality of applications, and is controlled by the service cooperation program 74 based on the cooperation information (see to FIG. 5) described in each application. Here, the cooperation information described in the three applications shown in FIG. 5, that is, "shopping support application is cooperable with migration support application", "migration support application is cooperable with shopping support application" and "health watch application is cooperable with each application in a parallel manner" are written in the nontransitory data area 86 as the cooperation information 88.

The combination and detailed information 90 is information indicating a combination (for example, "shopping support and migration support") that is arbitrarily selected from a plurality of cooperable applications (here, three applications shown in FIG. 5) and details of the combination (name of item want to buy, "wishing to decide while performing a migration", etc.), and is controlled by the service cooperation program 74 based on selection (input) by the user via a UI (described later) of FIG. 14-FIG. 16.

The user attribute information 92 is information indicating an attribute of the user, and shown in FIG. 7, a user (mobile terminal) ID (a, b, - - - ) and an attribute (walk impaired person, aged people, - - - ) are registered in association with each other.

The robot information 94 is information indicating an attribute, a function and a moving range of each of the various robots included in the robot service cooperation system 10 shown in FIG. 1, and as shown in FIG. 8, for example, a robot ID (R1, R2, R3, R4, - - - ), an attributes (wheelchair, humanoid, virtual, invisible, - - - ), a function ("wheelchair, talk", "guide, luggage carrier, talk", "health watch, talk", "person detection" - - - ) and a moving range ("in the shopping center", "in the shopping center", "within communicable range of mobile terminal", "fixed at the predetermined position of a shopping center", - - - ) are registered in association with each other.

The map information 96 includes wide area map information that covers an action range of the user (range including at least a house and a shopping center) and detailed map information relevant to the moving range (that is, shopping center) of the wheelchair robot 16*a* and the humanoid robot 16*b*. In addition to arrangement of the shops or stores and the counters in the shopping center, steps or rumps, obstacles, etc. that bar movement of the robot are also described in the detailed map information.

Figures 14, 15:
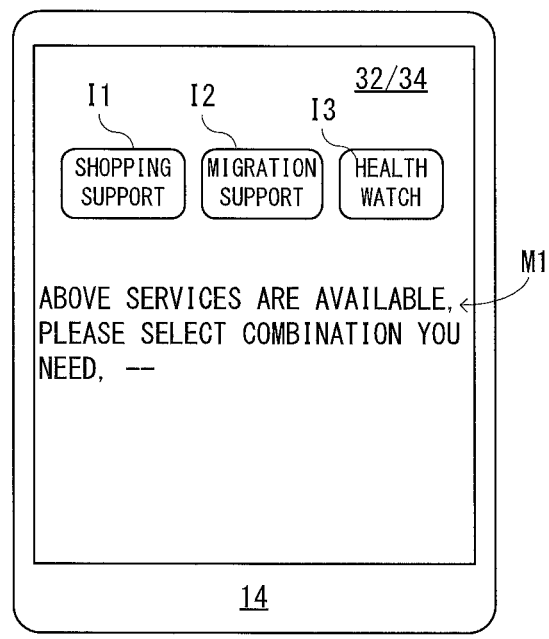
Figure 16:
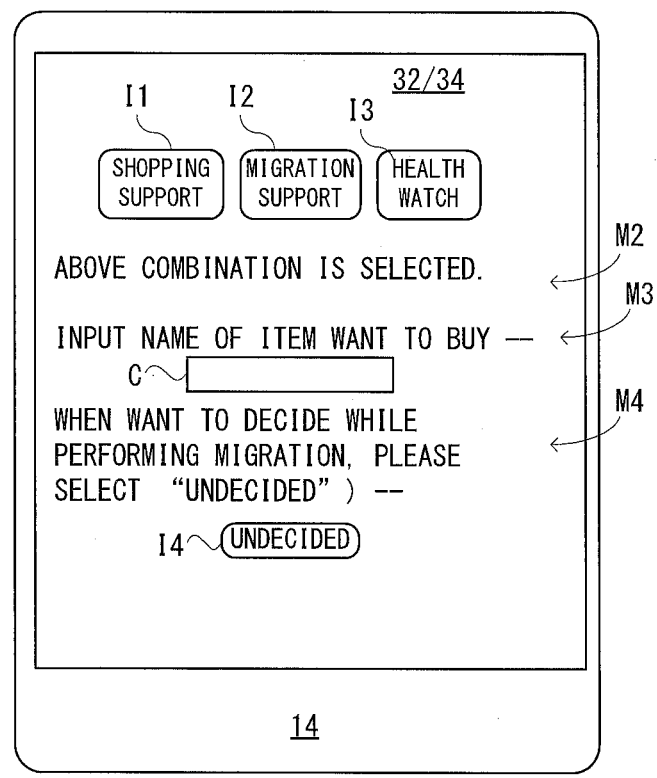
FIG. 16 is an illustration view showing a screen that makes a user input detailed information subsequently when a combination of shopping support and migration support is selected.

The UI image data 98 is image data for displaying a UI image as shown in FIG. 14-FIG. 16 on the touch screen of the mobile terminal 14. The UI image of FIG. 14 is for presenting a plurality of cooperable services that can be provided to the user (here, shopping support, migration support and health watch) and for making the user select a desired combination, and includes three icons I1-I3 respectively indicating the shopping support, migration support and health watch, and a message M1 to urge to select a desired combination (by a touch operation).

There are four (4) kinds of cooperable combinations as shown in FIG. 15(A)-FIG. 15(D) concerning the three services, the shopping support, the migration support and the health watch. If selecting a desired combination among these by a touch operation, display manners of the icon I1-I3 are changed such that selected state/nonselected state of each service can be understood. Here, the icon of the service in the selected state is as is the normal display, and the icon of the service in the nonselected state is changed to low-intensity (semi-transparent) display.

For example, if selecting a combination shown in FIG. 15(A), that is, the shopping support and the migration support are selected, the UI image of FIG. 14 is updated as shown by FIG. 16. The UI image of FIG. 16 is for making the user input subsequently detailed information relevant to the selected combination, that is, relevant to the combination of the shopping support and the migration support, and includes the icons I1-I3 similar to those of FIG. 15(A), a message M1 indicating that the combination of the shopping support and the migration support is selected, a message M2 to urge to input a name of item want to buy and an entry field C, a message M4 to urge to select "undecided" when wishing to decide while performing the migration and an icon 14 indicating "undecided".

If the user selects a desired combination and further inputs the detailed information relevant to the combination via the UI as shown in FIG. 14-FIG. 16, the combination and detailed information 90 is written in the nontransitory data area 86, and based on the combination and detailed information 90, the CPU 20 can produce the event queue information 84 as shown in FIG. 9(A)-FIG. 9(E).

Functional structure of the robot service cooperation platform (PF) implemented by the hardware (especially, the CPU 20 and the memory 26 of the server 12) of FIG. 1-FIG. 4 and the software of FIG. 5-FIG. 9 is shown in FIG. 10. With reference to FIG. 10, this PF is formed between an application layer L1 that the application A1 (shopping support application), the application A2 (migration support application), the application A3 (health watch application),—are belong to, a component layer L2 that a component C1 (transportation function of the wheelchair robot 16*a*), a component C2 (guide function of the humanoid robot 16*b*), a component C3 (detection function of the environment sensor 16*c*),—are belong to, and comprises a status management function F1, a position detection function F2, a service cooperation function F3, a database DB, event queue IC and user interface UI.

However, the user interface UI may belong to the component layer L2 as a UI component between the mobile terminal 14 and the user. Furthermore, a new application and a new component may be added to the application layer L1 and the component layer L2, respectively.

The status management function F1 is a function to manage the state of each of the robots, and controls the robot status information 80 and the service status information 82.

The position detection function F2 is a function to detect a current position of the user, and controls the current position information 78. The database DB stores various information that the service cooperation function F3 needs, here, the cooperation information 88, the user attribute information 92, the robot information 94 and the map information 96.

The event queue IC is for registering a service that a predetermined event is made to be a start condition (restart condition), and corresponds to the event queue information 84. The user interface UI is for presenting combinations of the cooperable services to the user and making the user select a desired combination, and controls the combination and detailed information 90. Then, the service cooperation function F3 implements the service cooperation as described above by registering the service into the event queue IC by using the status management function F1 and the position detection function F2 while referring to the database DB.

Processing (robot service cooperation processing) of the PF implemented by the CPU operation of the server 12 is shown in FIG. 11-FIG. 12. With reference to FIG. 11, the position detection function F1 (GPS circuit 46) detects in a step S1 the current position of the user (mobile terminal 14) that started to connect to the network 100. In a step S3, the CPU specifies a plurality of cooperable services that can be provided to the user based on the detected current position (current position information 78) of the user, the information in the database DB (the cooperation information 88, the user attribute information 92, the robot information 94 and the map information 96).

For example, when a user "a" who lives near the shopping center operates the mobile terminal 14 and accessed the robot service cooperation system 10, the user attribute information 92 indicates that the user is a walk impaired person. Furthermore, comparison of the current position information 78 and the map information 96 indicates that the current position of the user is inside the shopping center or near it. Then, if the robot information 94 is referred to, since the wheelchair robot 16a and the humanoid robot 16b are stationed in the shopping center, it is understood that the migration support application using the wheelchair robot 16a can be provided to the user at first, and further that the shopping support application using the humanoid robot 16b can be provided to the user.

Next, if the cooperation information 88 is referred to, it is understood that the migration support application and the shopping support application are cooperable mutually and that a health watch application is cooperable with the migration support application and the shopping support application in a parallel manner. Therefore, in this case, as the cooperable service that can be provided to the user "a", three services, the migration support, the shopping support and health watch are specified in the step S3.

When a user "b" who is an aged person (not a walk impaired person) accessed, since the migration support using the wheelchair robot 16a is unnecessary, two services, the shopping support and the health watch are specified in the step S3.

Next, it is determined in a step S5 whether a plurality of services are specified, and if NO, this robot service cooperation processing is terminated after shifting to a step S33 and performing other processing (for example, single service processing, error processing, etc.).

If YES in the step S5, the process proceeds to a step S7, and UI control is performed by using the UI image data 98, and displays a plurality of icons (I1, I2, - - - ) corresponding to a plurality of services specified in the step S3 on the touch screen of the mobile terminal 14, thereby to make the user select an arbitrary combination.

For example, when three services, the migration support, the shopping support and the health watch are specified in the step S3, the UI image as shown in FIG. 14 (that is, three icon I1-I3 indicating the three services, respectively and the message M1 to urge to select a desired combination) is displayed on the touch screen, and the user selects any one of the combinations of FIG. 15(A)-FIG. 15(D). Accordingly, the icon in the selected state is as is the normal display and the icon in the nonselected state becomes the low-intensity (semi-transparent) display.

Contrary to control of FIG. 15(A)-FIG. 15(D), the icon in the nonselected state may be as is the normal display and the icon in the selected state may be displayed with emphasis (contour enhancement, high intensity, etc.), or the icon of the nonselected state may be made the low-intensity display and the icon of the selected state may be emphasized.

Next, it is determined in a step S9 whether any one of the combinations is selected, and if NO here, this robot service cooperation processing is terminated after sifting to the step S33 and performing other processing (for example, error processing). If YES in the step S9, the process proceeds to a step S11 and a plurality of applications corresponding to the selected combination are activated in the mobile terminal 14.

Then, further UI control is performed in a step S13 so as to make the user input the detailed information relevant to the selected combination. For example, when the combination of the shopping and the migration is selected, the UI image as shown in FIG. 16 (that is, the message M2 that the combination of the shopping and the migration is selected, the message M3 to urge to input a name of an item want to buy and the entry field, the message M4 to urge to select "undecided" when wishing to decide while performing the migration, and the icon 14 indicating the "undecided") is displayed on the touch screen, and the user inputs a name of the item if the item want to buy is decided, but otherwise, the user selects "undecided" (if wishing to decide while performing the migration).

If the combination is thus selected and the detailed information relevant to the combination is further input (selected), the combination and detailed information 90 is stored in the nontransitory data area 86 (registered in the database DB).

Next, it is determined in a step S15 whether the detailed information is input (selected) based on existence of the combination and detailed information 90, and if NO here, the robot service cooperation processing is terminated after shifting to the step S33 and performing other processing (for example, error processing). If YES in the step S15, the process proceeds to a step S17.

With reference to FIG. 12, a cooperation manner of a plurality of services that constitute the selected combination is decided in the step S17 based on the cooperation information 88 and the combination and detailed information 90. For example, when the combination of the shopping and the migration is selected and also a name of an item such as a "book" is input, the cooperation manner of the shopping and the migration is decided as "sequential." When the combination of the shopping and the migration is selected and also "undecided" is selected, a cooperation manner of the shopping and the migration is decided as "interruption." The cooperation manner of the shopping and/or the migration and the health watch is always "parallel."

Then, the process proceeds to a step S19, and the start conditions (further the restart conditions in a case of the interruption manner) of the respective services are registered in the event queue IC according to the decided cooperation manner. For example, when making the shopping and the migration cooperate in the sequential manner, as shown in FIG. 9(A), in the event queue IC, "Arrived at shopping center" is registered as the start condition for the shopping support, and further "Shopping finished" is registered as the start condition of the migration support. When making the shopping support and the migration support cooperate in the interruption manner, as shown in FIG. 9 (B), "Arrived at shopping center" is registered as the start condition for the migration support, and further "Migration interrupted" is registered as the start condition for the shopping support, and then, "Shopping finished" is registered as the restart condition for the migration support.

Furthermore, when making the shopping support (or the migration support) cooperate with the health watch in the parallel manner, in the event queue IC, as shown in FIG. 9 (C), "Arrived at shopping center" is registered as the start condition for the shopping support (or the migration support), and further "Shopping (or Migration) started" is registered as the start condition for the health watch.

When making the shopping support and the migration support cooperate in the sequential manner, and further making the health watch cooperate in the parallel manner, as shown in FIG. 9(D), "Arrived at shopping center" is registered as the start condition for the shopping support and "Shopping finished" is registered as the start condition for the migration support, in addition thereto, "Shopping started" may be registered as the start condition for the health watch.

Similarly, when making the shopping support and the migration support cooperate in the interruption manner, and further making the migration support cooperate in the parallel manner, as shown in FIG. 9(E), "Arrived at shopping center" is registered as the start condition for the migration support, and further "Migration interrupted" is registered as the start condition for the shopping support, and then, "Shopping finished" is registered as the restart condition the migration support, in addition thereto, "Migration started" may be registered as the start condition of the health watch.

Next, it is determined in a step S21 whether there is any service that reaches the start condition (or restart condition) in the registered services of the event queue IC with reference to the service status information 82 (using the status management function). If NO here, the same determination is repeated after a predetermined waiting time.

If YES in the step S21, the process proceeds to a step S23, and the resource (robot or component) required for the service is assigned. The robot status information 80 is updated according to this. Then, the process proceeds to a step S27, after notifying having assigned the resource to the application corresponding to the service in the step S25.

In the step S27, it is determined whether there is any service ended (or interrupted) based on the service status information 82. If NO here, the process returns to the step S21 and repeating the same processing as the above. If YES in the step S27, the process proceeds to a step S29 and releasing the resource currently assigned to the ended (or interrupted) service. The robot status information 80 is updated according to this.

Then, it is determined in a step S31 whether all the registered services in the event queue IC are ended, and if NO here, the process returns to the step S21 and repeating the same processing as the above. If YES in the step S31, the process returns to the step S1 and repeating the same processing as the above.

Processing of each application (A1, A2, - - - ) implemented by an operation of the CPU of the server 12 is shown in FIG. 13. This processing may be performed by a further server (not shown) on the network 100. With reference to FIG. 13, it is determined in a step S51 whether there is any notification having assigned the resource from the PF, and if NO here, the same determination is repeated after a predetermined waiting time. If YES in the step S51, the service is started by using the assigned resource. Then, the process proceeds to a step S55.

In the step S55, it is determined whether the service is ended (or interrupted), and if NO here, the process returns to the step S55 and repeating the same determination.

If YES in the step S55, the process proceeds to a step S57, and completion (or interruption) of service is notified to the PF. The service status information 82 is updated according to this. Then, the process returns to the step S51 and repeating the same processing as the above.

As described above clearly, the robot service cooperation system 10 of this embodiment includes the server 12 that is connected to the network 100, the mobile terminal 14 that is connected to the network 100 and various robots 16a-16c that are connected to the network 100, and the CPU 20 of the server 12 makes a plurality of services that a plurality of applications software (hereinafter, "applications") A1-A3 on the network 100 respectively provide to the user of the mobile terminal 14 by using various robots 16a-16c cooperate mutually as follows.

More specifically, the cooperation information indicating which other application can be cooperated with is described in each application A1-A3 (FIG. 5), and the CPU 20 specifies (S3) a plurality of cooperable services that can be provided to the user of the mobile terminal 14 at least based on the cooperation information described in each application A1-A3, presents to the user of the mobile terminal 14 a plurality of specified services via the touch screen (UI as shown in FIG. 14-FIG. 16) so as to make the user select an arbitrary combination (S7, S13), and then, makes a plurality of services that constitute the selected combination cooperate mutually by registering at least a start condition of each service into the event queue IC in association with at least an end event of each other service (S17, S19: FIG. 9(A)-FIG. 9(E)). Therefore, it is possible to provide a plurality of services that the user needs with making them cooperate mutually in at least a sequential manner.

Specifically, the CPU 20 makes the user further input the information (detailed information) relevant to the selected combination (S13: FIG. 16), and when the information (for example, name of item want to buy) that it is possible to determine that the first service (shopping support) and the second service (migration support) should be sequentially performed, based on the information concerned, the start condition of the second service (migration support) is registered in association with the end event of the first service (shopping support) (FIG. 9(A)). Accordingly, it is possible to provide the two services that the user needs with making them cooperate in a sequential manner. In general, if the start condition of the i-th service is registered in association with the end event of the (i−1)th service, it is possible to make i units of services cooperate in a sequential manner (here, i is an integer greater than or equal to 2).

Furthermore, when inputting the information (for example, "having not yet decided item want to buy", "wishing to decide item want to buy while performing migration", etc.) that it is possible to determine that the second service (shopping support) should be performed during performance of the first service (migration support), based on the information concerned, the CPU 20 registers the start condition of the second service (shopping support) in association with the interruption event and the restart condition of the first service (migration support) is registered in association with the end event of the second service (shopping support) (FIG. 9(B)). Accordingly, it is possible to provide the two services that the user needs with making the services cooperate in a manner that the user desires among the sequential manner and the parallel manner.

Furthermore, it is described in the cooperation information of a specific application (health watch application A3) that the application concerned can be cooperated with any further application (shopping support application A1, migration support application A2) in the parallel manner, and when the service (health watch) provided by the specific application is included in the plurality of services that constitute the selected combination, the start condition of the service concerned is registered in association with the start event of the further service (shopping, migration) (FIG. 9(D), FIG. 9(E)). Accordingly, it is possible to provide the further service in the parallel manner with making the two services cooperate in the sequential manner or the parallel manner.

The end/interruption event of the service is issued from the application that provides the service concerned (or from the robot or component utilized by this application), for example. Otherwise, the event may be issued from the mobile terminal 14 according to the operation by the user.

Furthermore, in the nontransitory data area 86 of the memory 26, the user attribute information 92 (FIG. 7) indicating the attribute of the user, and the robot information 94 (FIG. 8) at least indicating functions of various robots are stored (registered in the database DB), in specifying (step S3) a plurality of cooperable services that can be provided to the user, the CPU 20 refers to the user attribute information 92 and the robot information 94 in addition to the cooperation information described in each application A1-A3. In addition, each of the information is preferably registered such that it can be updated. Accordingly, it becomes possible to provide the service using the robot that has the function according to the attribute of the user.

Preferably, the robot information 94 further indicates a moving range of the robot. In this case, the CPU 20 detects the current position of the user by the GPS circuit 40, and specifies the service by taking into consideration the comparison result of the detection result and the moving range of the robot. Accordingly, it becomes possible to provide the service using the robot in various places.

Furthermore, in presenting a plurality of specified services (shopping support, migration support and health watch, for example), the CPU 20 displays corresponding a plurality of icons (three icons I1-I3, for example) on the touch screen (thing that the touch panel 34 is formed on the display surface of the display 32) and makes the user select an arbitrary combination (FIG. 14, FIG. 15), and makes a display manner mutually differ between a plurality of first icons (I1, I2) and a remaining second icon (I3) (FIG. 16) among the plurality of icons displayed on the touch screen. Accordingly, it is possible to make the user recognize whether the service in a selected state or a non-selected state. As a result, the user can know existence of the service that the user has not selected until now, and can also mutually switch the selected or non-selected state of each service.

Although the processing (step S7) that presents to the user a plurality of services and makes the user select the arbitrary combination is performed the touch screen of the mobile terminal 14 in this embodiment (utilizing UI as shown in FIG. 14-FIG. 16), the processing may be performed by using a voice output function and a voice recognition function of the mobile terminal 10 or various robots (16a, 16b). For example, there is a method that the CPU 50 of the humanoid robot 16b outputs from the speaker 38 a voice that presents a plurality of cooperable services that can be provided to the user, and asks the user to select a desired combination, and the utterance voice of the user is captured the microphone 36 and recognized.

Furthermore, although the detection (step S1) of the current position of the user (mobile terminal 14) is performed in this embodiment by using the GPS, instead of this or in addition to this, the position detection function of the network 100 may be used.

Although there was described as above a case where a plurality of services are provided to a single user, in other word, a case where the services are cooperated mutually in the situation that there are resources enough to the number of users and competition does not occur among users, when providing a plurality of services to a plurality of users, it is necessary to register the services to be provided to each user in the event queue while avoiding (mediating) the resource competition between the users.

DESCRIPTION OF REFERENCE NUMERALS

10—robot cooperation system
12—server
14—mobile terminal (virtual robot)
16a—wheelchair robot
16b—humanoid robot
16c—environment sensor (invisible robot)
20, 30, 50—CPU
22, 32—display
26, 42, 60—memory
34—touch panel
100—network

The invention claimed is:

1. A robot service cooperation system that includes a server connected to a network, a mobile terminal connected to the network and a robot connected to the network, and makes a plurality of services cooperate mutually, the plurality of services being respectively provided to a user of the mobile terminal by a plurality of applications software on the network by using the robot,
wherein cooperation information indicating which another application software can be cooperated with is described in each of the applications software, and
the server comprises
a specifying module operable to specify a plurality of cooperable services that can be provided to the user of the mobile terminal at least based on the cooperation information described in each of the service applications software;
a presentation selection module operable to present to the user of the mobile terminal a plurality of services that are specified by the specifying module and make the user select an arbitrary combination of the services; and
a cooperation module operable to make a plurality of services constituting the combination that is selected by the presentation selection module cooperate mutually by registering at least a start condition of each of the plurality of services into an event queue in association with at least an end event of another service;

wherein the presentation selection module includes an input module operable to make the user of the mobile terminal further input information relevant to the selected combination, and the cooperation module is operable to register, when the input module inputs information that it is possible to determine that a first service and a second service should be sequentially performed, a start condition of the second service in association with an end event of the first service based on the information concerned.

2. The robot service cooperation system according to claim 1, wherein the cooperation module is operable to register, when the input module inputs information that it is possible to determine that the second service should be performed with interrupting performance of the first service, a start condition of the second service in association with an interruption event of the first service and a restart condition of the first service in association with an end event of the second service based on the information concerned.

3. The robot service cooperation system according to claim 1, wherein it is described in the cooperation information of a specific application software that the application software concerned can cooperate with any further application software in a parallel manner, and the cooperation module is operable to register, when the service provided by the specific application software is included in the plurality of services that constitute the combination selected by the selection module, a start condition of the service concerned in association with a start event of the further service.

4. The robot service cooperation system according to claim 1, further comprising a database that is registered with user attribute information indicating the attribute of the user of the mobile terminal and robot information indicating at least a function of the robot, wherein the specifying module is operable to perform specifying by referring also to each information in the database.

5. The robot service cooperation system according to claim 4, wherein the robot information further indicates a moving range of the robot, and further comprising a detection module operable to detect a current position of the user of the mobile terminal, and the specifying module is operable to perform specifying while also taking into consideration a comparison result of a detection result by the detection module and the moving range of the robot.

6. The robot service cooperation system according to claim 1, wherein the presentation selection module is operable to display a plurality of icons corresponding to the plurality of services specified by the specifying module on a touch screen of the mobile terminal, and make the user select an arbitrary combination, and make display manners mutually differ between a plurality of first icons constituting the selected combination and a remaining second icon among the plurality of icons being displayed on the touch screen.

* * * * *